US006551233B2

(12) United States Patent
Perreault et al.

(10) Patent No.: US 6,551,233 B2
(45) Date of Patent: Apr. 22, 2003

(54) MAGNETIC STIMULATOR POWER AND CONTROL CIRCUIT

(75) Inventors: David J. Perreault, Brookline, MA (US); Scott Mogren, Holliston, MA (US)

(73) Assignee: R. B. Carr Engineering, Onc., Newton, MA (US)

( * ) Notice: Subject to any disclaimer, the term of this patent is extended or adjusted under 35 U.S.C. 154(b) by 41 days.

(21) Appl. No.: 09/924,907

(22) Filed: Aug. 8, 2001

(65) Prior Publication Data

US 2003/0032852 A1 Feb. 13, 2003

(51) Int. Cl.$^7$ .............................. A61N 2/00; G01R 27/28
(52) U.S. Cl. .............................. 600/9; 324/657; 324/673
(58) Field of Search ................................ 324/322, 414, 324/600–727; 600/9–15

(56) References Cited

U.S. PATENT DOCUMENTS

| 4,039,939 A | * | 8/1977 | Wagner ...................... 324/611 |
| 4,638,670 A | * | 1/1987 | Moser .......................... 73/658 |
| 5,285,161 A | * | 2/1994 | Rzedzian et al. ............ 324/322 |
| 5,479,102 A | * | 12/1995 | El-Hamamsy et al. ...... 324/414 |

OTHER PUBLICATIONS

Dvorak, J. et al. "Motor Evoked Potentials by means of Magnetic Stimulation in Disorders of the Spine," Methods in Clinical Neurophysiology, vol. 3 No. 3 (Jul. 1992), pp. 45–64.

Eisen, A. "Cortical and Peripheral Nerve Magnetic Stimulation," Methods in Clinical Neurophysiology, vol. 3 No. 4 (Dec. 1992), pp. 65–84.
Pascual–Leone, A. et al. "Safety of rapid–rate transcranial magnetic stimulation in normal volunteers," Electroencephalographyand Clinical Neurophysiology, vol. 89 (1993), pp. 120–130.
"MagPro Magnetic Stimulator Instruction Manual," DANTEC Medical A/S, Nov. 1992, pp. 1–15.
"Magnetic Stimulator MagPro Service Manual & Circuit Diagrams," DANTEC Medical A/S, Feb. 1993, pp. 1–38.
"Magnetic Stimulator Accessories for MagPro," DANTEC Medical A/S, four pages.
"Magnetic Coil Transducer MC125 used with MagPro," DANTEC Medical A/S, Aug. 1993, two pages.
"Magnetic Coil Transducer MC–B70 used with MagPro," DANTEC Medical A/S, Aug. 1993, two pages.

* cited by examiner

Primary Examiner—Max F. Hindenburg
Assistant Examiner—Nikita Veniaminov
(74) Attorney, Agent, or Firm—Weingarten, Schurgin, Gagnebin & Lebovici LLP

(57) ABSTRACT

An electromagnetic stimulator circuit has a precharge power supply, a capacitor, a set of switches, and a stimulator coil. The switches, which can be implemented using a variety of devices, enable flexible control over the coil current waveform without requiring the physical reconfiguration of circuit elements. The shape of the output current pulse is controlled by the modulation of the switches, and much of the energy applied to the coil is returned from the coil to the capacitor for reuse on the succeeding pulse. Less power is required and less heat energy is generated.

18 Claims, 7 Drawing Sheets

MAGNETIC STIMULATOR POWER AND CONTROL CIRCUIT

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

Magnetic stimulator systems have a wide range of medical applications, including transdermal nerve stimulation. In many cases a monophasic stimulus is desired, in which each magnetic pulse in a pulse train has a rapid rise and a slow fall. In contrast, a pulse having similar rise and decay rates is referred to as being biphasic.

The general prior art approach for generating such pulses is illustrated in FIG. 1. A stimulus coil 12 acts as an inductance in the circuit 10, and the magnetic field at the coil 12, which is proportional to the coil current, is the output stimulus. A pre-charging power supply 14 charges a capacitor C to a predetermined voltage. A switch $S_1$ is used to connect the coil 12 across the capacitor C, causing an LC oscillation with a fast current rise in the coil 12. When the capacitor 16 voltage reaches zero, at which point the coil 12 current will be near its peak, a second switch $S_2$ is closed bringing a resistor R into the circuit, causing an LCR resonant decay with a slow fall time.

The magnitude of the current pulse in the coil 12, and thus the resulting magnetic field, is determined by the capacitor C pre-charge voltage. The relative rate of rise and fall of the current, and the shape of the pulse, is determined by the values of the fixed circuit elements, such as the coil 12 inductance, the capacitance of capacitor C, and the resistance of resistor R. All of the capacitor C pre-charge energy is dissipated in the resistor R, coil 12, and switches $S_1$, $S_2$.

One embodiment 20 of this prior art approach, used in the MagPro magnetic stimulator by Medtronic, Inc., Minneapolis, Minn. (formerly Dantec Medical A/S), is illustrated in FIG. 2. Values for the circuit components are: C=180 $\mu$f; $L_{coil}\approx 11$ $\mu$H; and R$\approx$60–90 m$\Omega$. This system uses a thyristor 24 as the first switch, and a diode 22 as the second switch, providing simple, static control over the coil 28 pulse shape out of the pre-charge power supply 26. Coil current and voltage waveforms with a 220 Vac input pre-charge power supply 26 are shown in FIG. 7.

The prior art approach to generating the desired waveform, while being simple and straightforward, has two serious deficiencies. First, the capacitor pre-charge energy for each pulse is entirely dissipated in the circuit elements, thus requiring a pre-charging power supply that draws a large amount of power from the utility or other source. For many practical applications, the amount of power required for desired pulse magnitudes and repetition rates is greater than can be drawn from a conventional 15 A, 110 V outlet, thus necessitating either a higher-voltage or higher-current utility outlet. Furthermore, the dissipated power results in a large amount of heat loss into the environment which is undesirable and potentially unsafe.

A second deficiency associated with the prior art approach is that the pulse shape and duration at the coil is determined entirely by the values of the constituent circuit elements, values which cannot be adjusted dynamically. In order to enable flexible or adaptive control over the resulting waveform, either monophasic or biphasic, accurate dynamic adjustment of stimulator circuit characteristics such as the relative rise and fall rates of the circuit current must be enabled.

BRIEF SUMMARY OF THE INVENTION

A new stimulator circuit 100 that overcomes the limitations of the prior art is disclosed. The general structure of the present invention is illustrated in FIG. 3. The system 100 has a pre-charge power supply 102, a capacitor C, a set of switches $S_1$, $S_2$, $S_3$, and $S_4$, and a stimulator coil 104. The switches, which can be implemented using a variety of devices as discussed in detail below, enable flexible control over the coil current waveform without requiring the physical reconfiguration of circuit elements. The switches and coil may be collectively referred to as a coil switching circuit 106.

Certain common reference designators are used in multiple drawings, such as the legends "C" and "$S_1$," though this is merely for convenience and is not to imply that the devices so designated are necessarily the same in each illustrated embodiment.

In the presently disclosed invention, the shape of the output current pulse is controlled by the modulation of the switches $S_1$ through $S_4$. This contrasts with the prior art, in which the current pulse shape is determined only by the values associated with constituent circuit elements and in which current rise time is not dynamically controllable. Furthermore, with the presently disclosed circuits and methods, much of the energy (limited by parasitic losses in the coil, switching devices, etc.) is returned from the coil to the capacitor for reuse on the succeeding pulse. The presently disclosed invention thus has lower power requirements and produces less heat as compared to the prior art.

BRIEF DESCRIPTION OF THE SEVERAL VIEWS OF THE DRAWING

The invention will be more fully understood by reference to the following Detailed Description of the Invention in conjunction with the drawings of which.

DETAILED DESCRIPTION OF THE INVENTION

Figure 8:
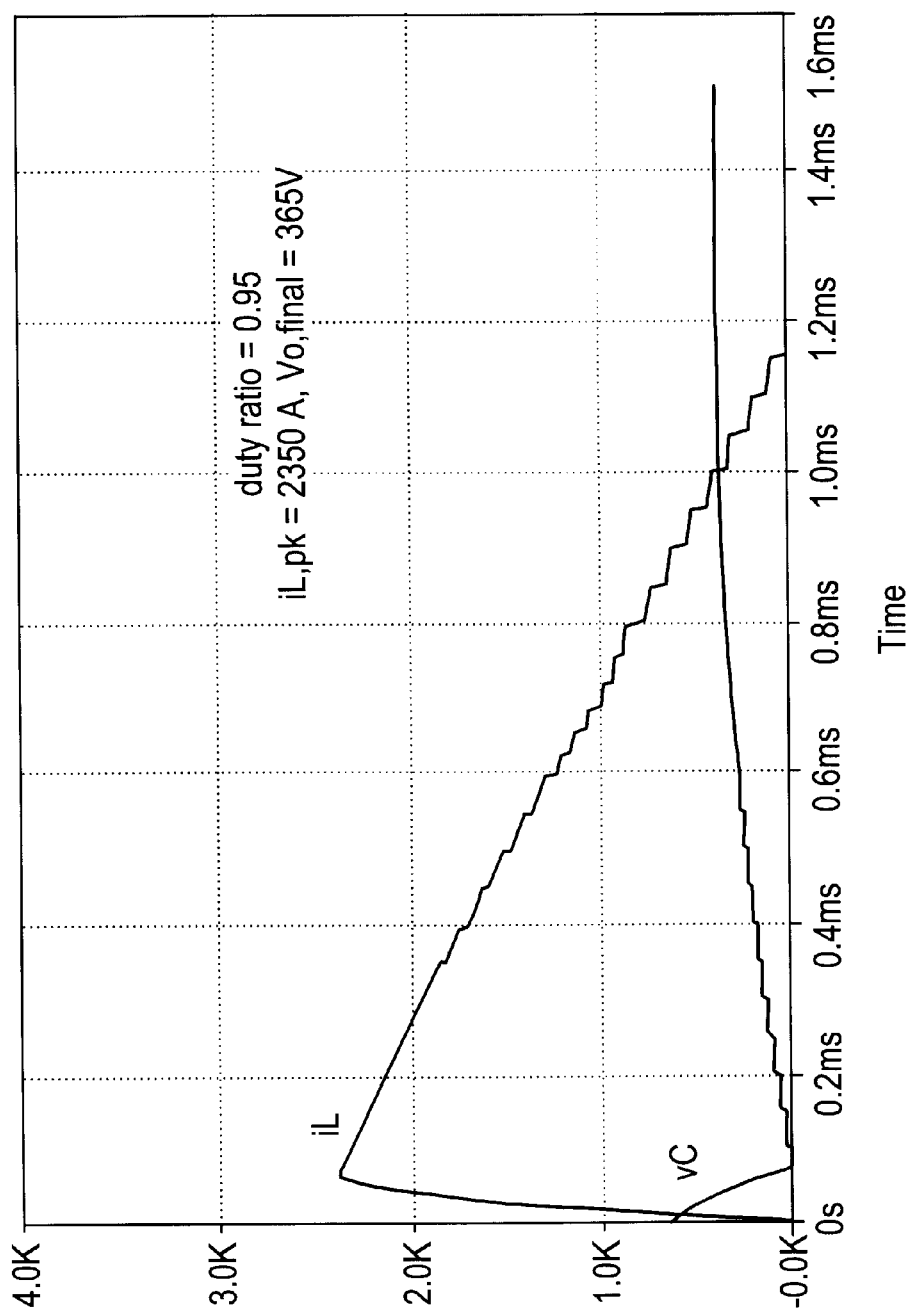
FIG. 8 illustrates coil current and capacitor voltage as a function of time with one switch in the generalized magnetic stimulator circuit of FIG. 3 switched at a 0.95 duty ratio.
Figure 9:
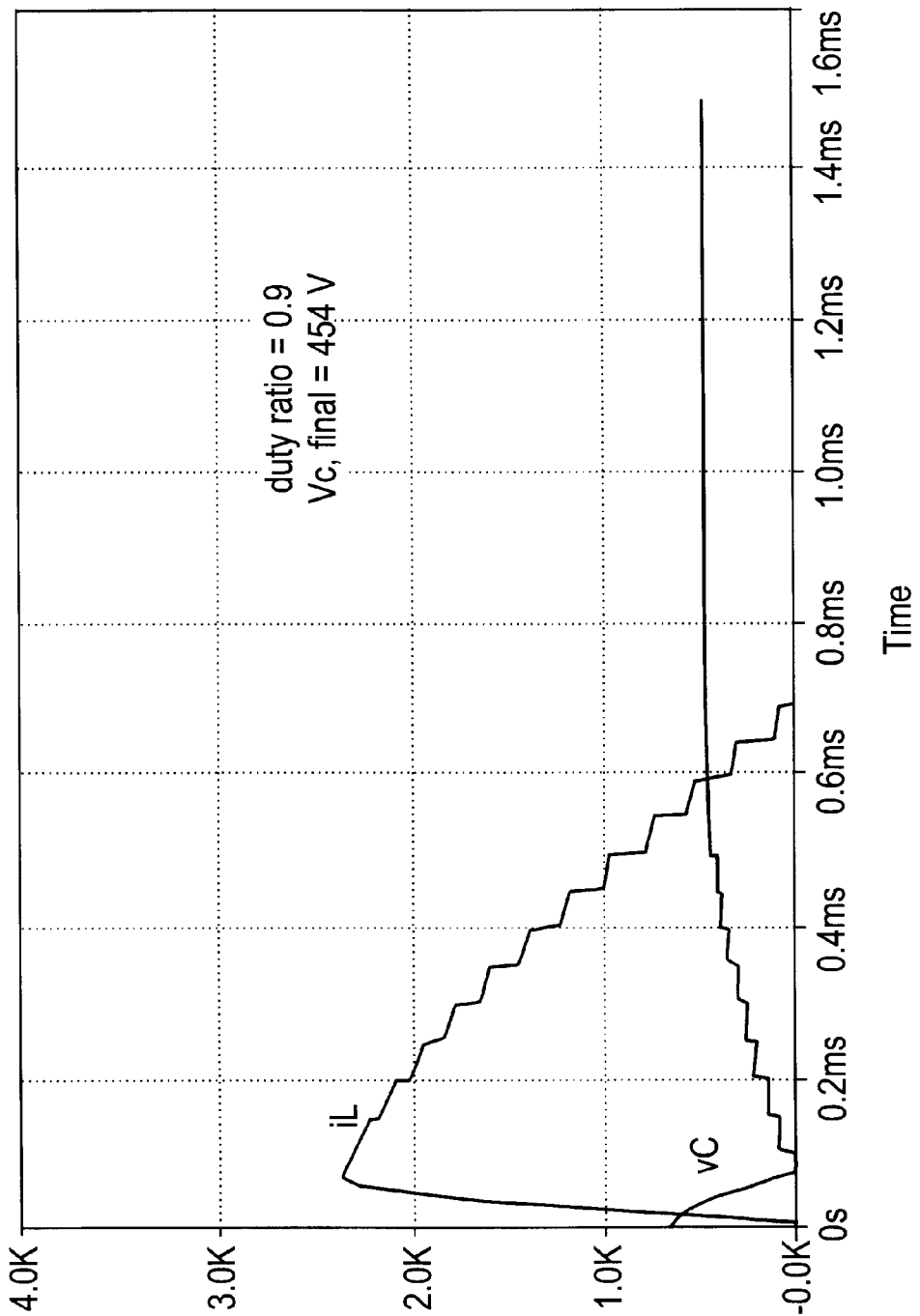
FIG. 9 illustrates coil current and capacitor voltage as a function of time with one switch in the generalized magnetic stimulator circuit of FIG. 3 switched at a 0.90 duty ratio.
Figure 10:
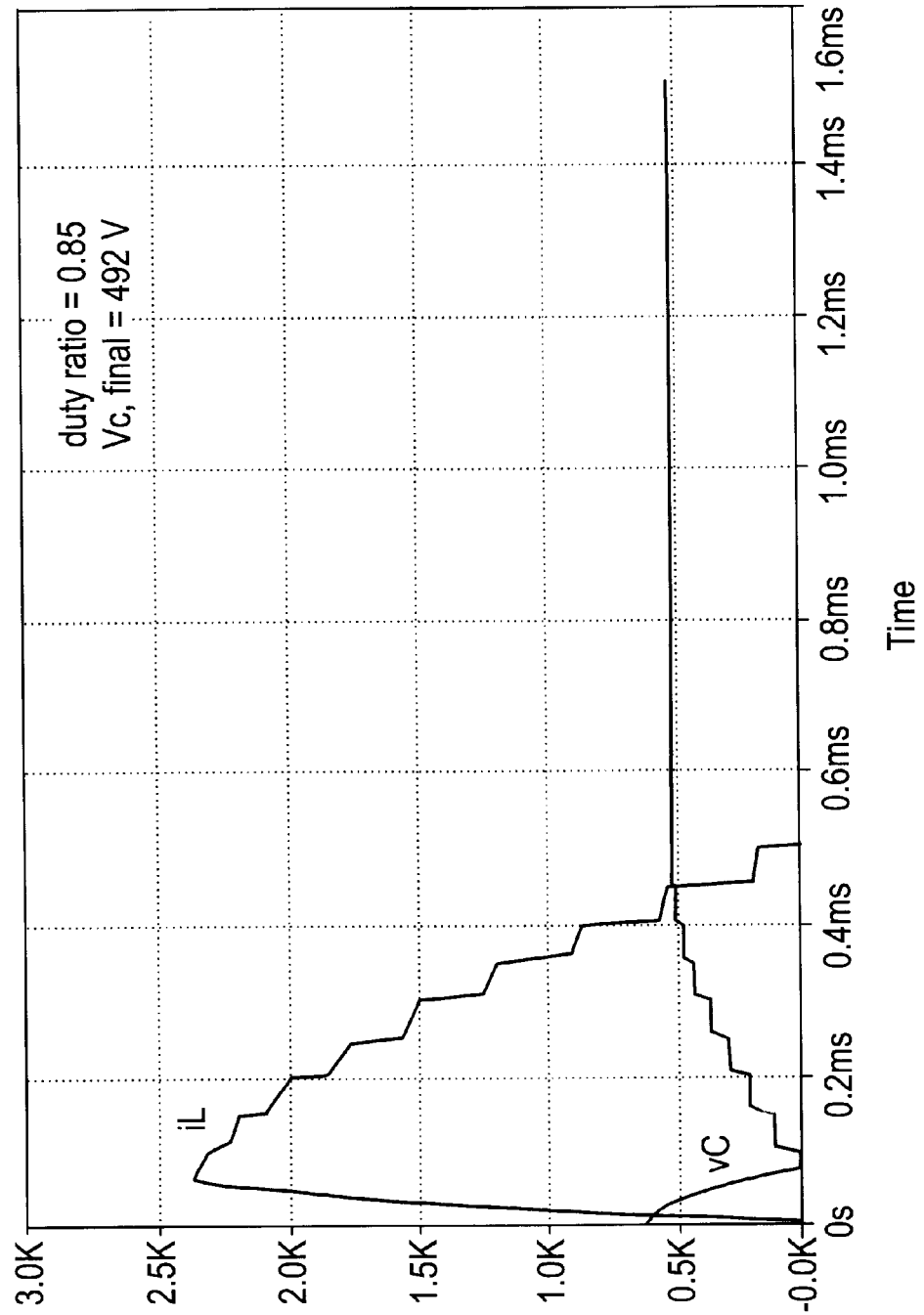
FIG. 10 illustrates coil current and capacitor voltage as a function of time with one switch in the generalized magnetic stimulator circuit of FIG. 3 switched at a 0.85 duty ratio.

Operation for generation of a single pulse using the presently disclosed coil switching circuit 106 is as follows. The capacitor C is pre-charged by the power supply 102 to a specified voltage with $S_1$ through $S_4$ "off," or open. Any suitable capacitor pre-charge circuit 102 may be employed for this purpose. For proof-of-concept purposes, the capacitor was pre-charged to 600V. A pulse is then initiated by turning $S_1$ and $S_2$ "on," i.e. switching them to a closed state, a step which initiates an LC ring with a fast current rise rate, such as shown in FIGS. 8 through 10. The peak current as tested approached 2400 A. For simplicity, control elements which regulate the operation of the switches are omitted in FIG. 3.

In certain embodiments, biphasic pulses are desired. To this end, the current rise rate, as well as the rate of discharge of the capacitor C voltage, can be controlled by modulating between either $S_1$ and $S_3$ or $S_2$ and $S_4$, or modulating both sets of switches at the same time, with controlled duty ratio(s) d at a frequency greater than the resonant frequency. Specifically, the modulation can be achieved by rapidly switching between $S_1$ being on, then $S_3$ being on while $S_1$ is off, where $S_1$ is on for a controlled fraction of the time d. Alternatively, $S_1$ and $S_2$ may be left on during the pulse rise to achieve the fastest rise time (d=1).

Once the coil 104 current and/or capacitor C voltage reach a desired level (e.g., the capacitor voltage reaches zero), a new operating mode is entered for a controlled fall of the coil 104 current and recharge of the capacitor C. In one embodiment, $S_1$ is turned off and $S_3$ is turned on, then $S_2$ and $S_4$ are alternately modulated with a controlled duty ratio. In another embodiment, $S_2$ is turned off and $S_4$ is turned on, then $S_1$ and $S_3$ are alternately modulated with a controlled duty ratio. Further still, one embodiment may modulate both sets of switches ($S_1/S_3$, $S_2/S_4$) at the same time.

To control the rate of fall of the current and field, the switches are modulated with controlled duty ratio(s) at a frequency greater than the natural oscillation frequency of the LC circuit. For example, in one embodiment, $S_1$ is turned off, $S_3$ is turned on, then control is provided to rapidly switch between $S_2$ being on and $S_4$ being on, with $S_2$ on for a fraction of time d. With this switching pattern, the average rate at which the current in the coil 104 falls can be controlled by the duty ratio d. The energy in the coil 104 is returned to the capacitor C, except for losses in the devices and the coil 104 resistance. Once the coil 104 current reaches zero, the switches $S_1$ through $S_4$ are turned off.

FIGS. 8 through 10 illustrate the impact on coil current (iL) and capacitor charge state (vC) as a function of time for duty ratios of 0.95, 0.90, and 0.85, respectively. It has been established that with a higher duty ratio, the decay time is greater and the percentage of energy recovered in the capacitor is lower compared to that with a lower duty ratio. This results from increased conduction losses due to the increased decay time. In each of FIGS. 8–10, the peak inductor current reached approximately 2350 A. A duty cycle of 0.95 resulted in a final capacitor voltage of 365 V (FIG. 8). A duty cycle of 0.90 resulted in a final capacitor voltage of 454 V (FIG. 9). A duty cycle of 0.85 resulted in a final capacitor voltage of 492 V (FIG. 10).

Thus, it is expected that, for each application, a point of optimization will need to be established between decay time and energy recovery efficiency. Controlling the duty ratio as a function of capacitor voltage and/or inductor current may be useful in recovering additional energy for a given current waveform slope, but it is believed that the improvement may not be overly significant.

Similar switch control techniques, including hysteresis current control over the coil current, peak current control, or average current control, can be used to control the switches with similar effect.

Figure 1:
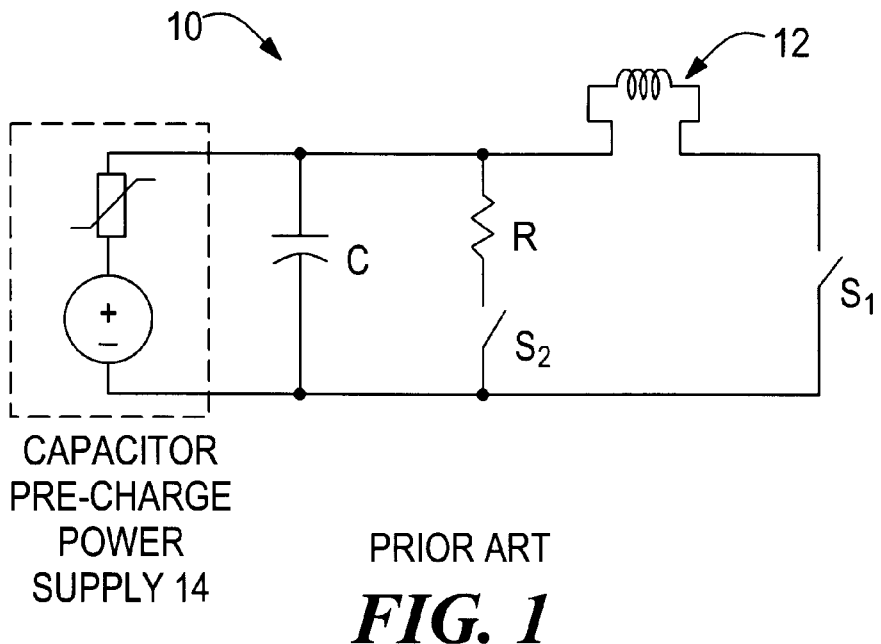
FIG. 1 is a schematic view of a magnetic stimulator circuit according to the prior art.
Figure 2:
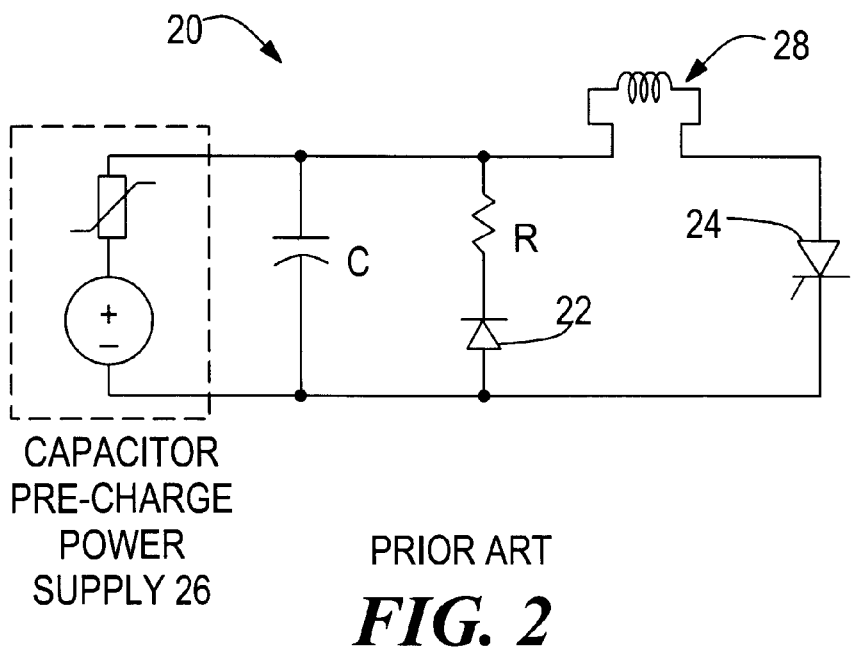
FIG. 2 is a schematic view of a specific embodiment of a magnetic stimulator circuit according to the prior art.
Figure 3:
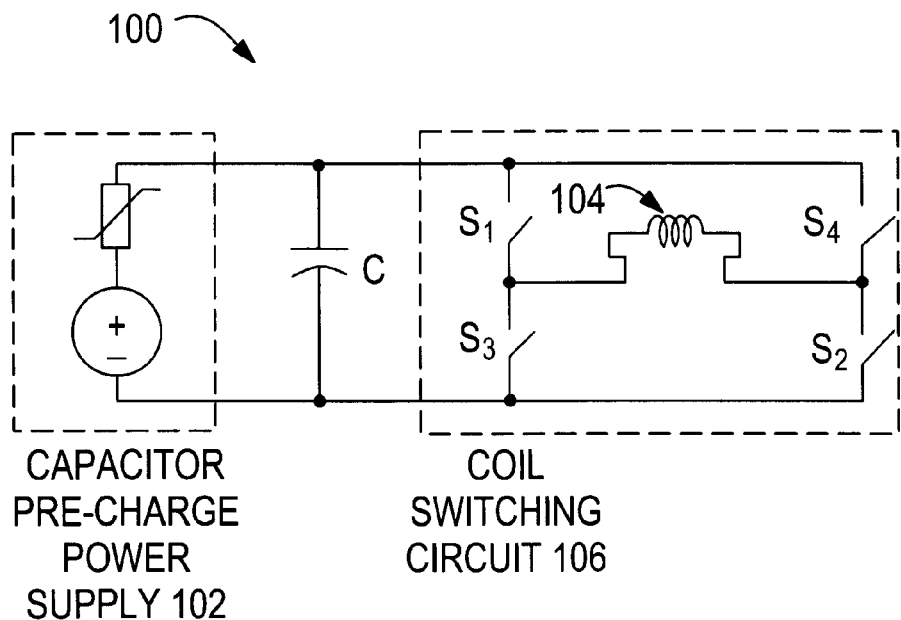
FIG. 3 is a schematic view of a magnetic stimulator circuit according to the presently disclosed invention.
Figure 4:
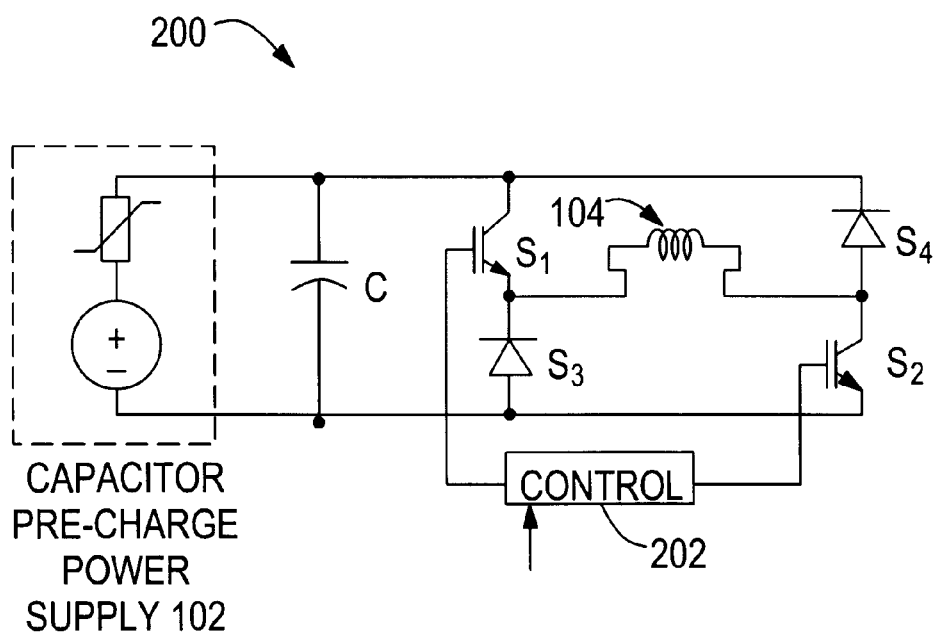
FIG. 4 is a schematic view of a first embodiment of the magnetic stimulator circuit of FIG. 3.
Figure 5:
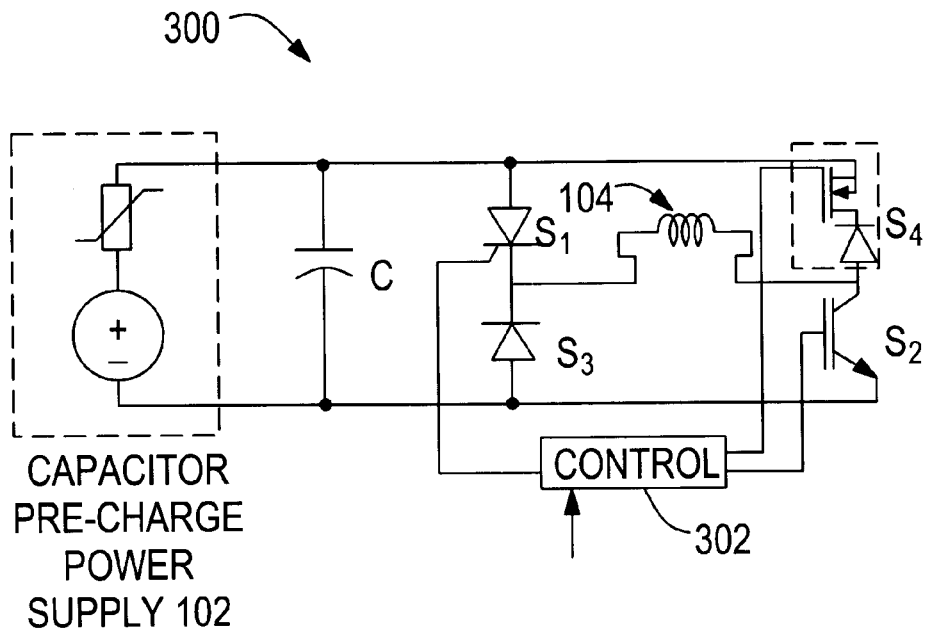
FIG. 5 is a schematic view of a second embodiment of the magnetic stimulator circuit of FIG. 3.
Figure 6:
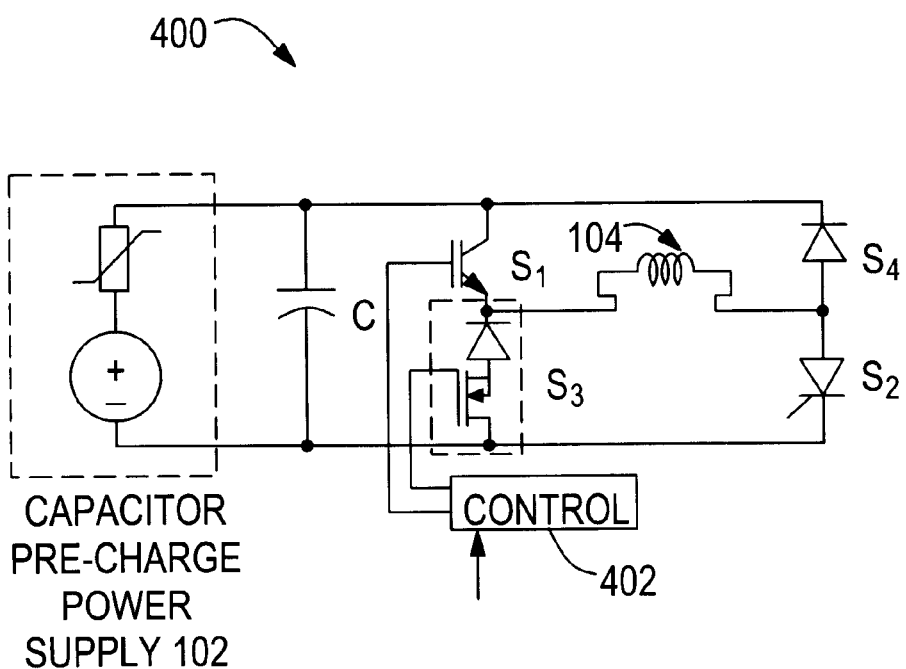
FIG. 6 is a schematic view of a third embodiment of the magnetic stimulator circuit of FIG. 3.
Figure 7:
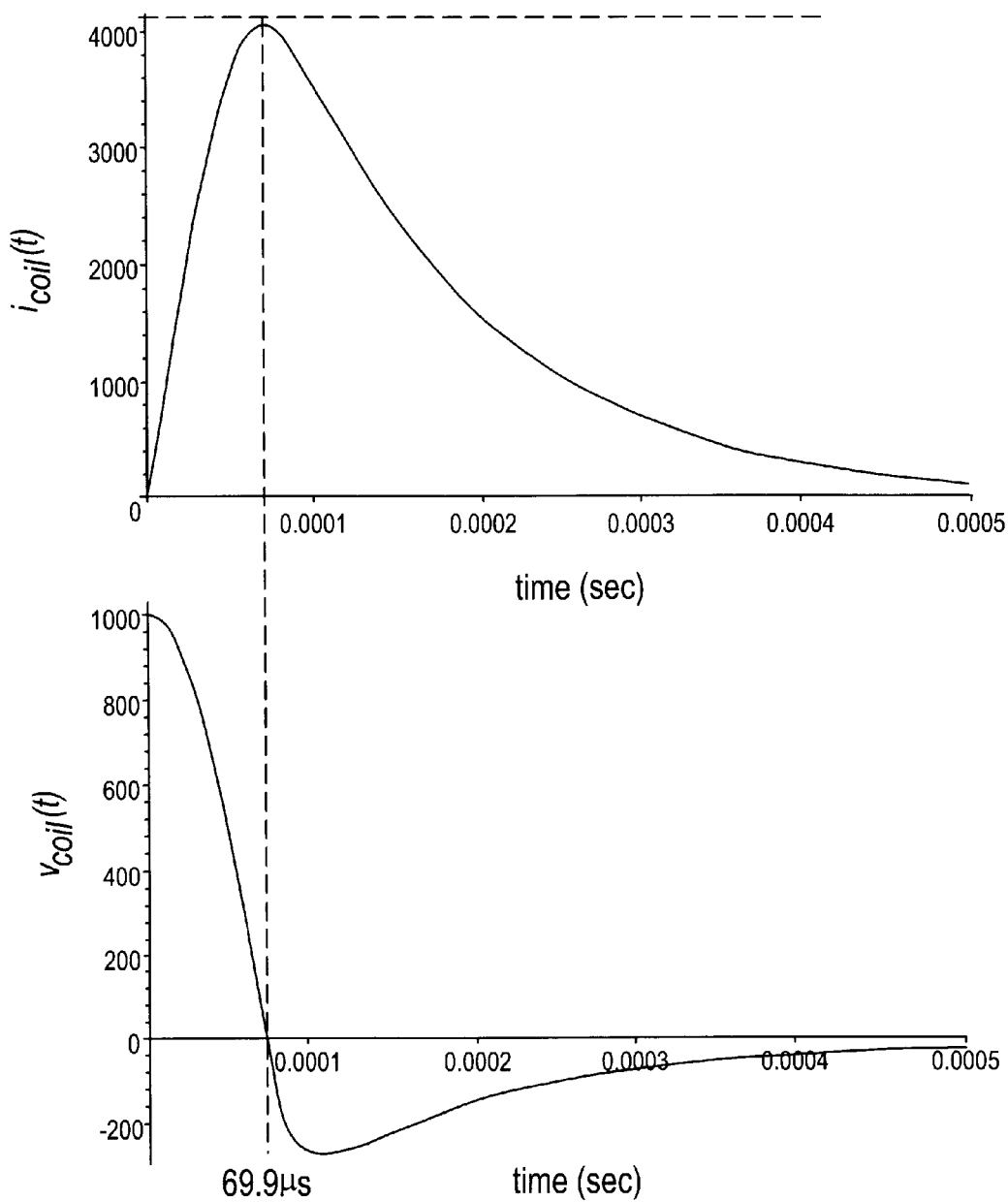
FIG. 7 illustrates prior art coil current and voltage as a function of time.

For simplicity, the box 106 is not shown in FIGS. 4–6, though in each illustrated embodiment, the switches $S_1$ through $S_4$ and the coil 104 comprise particular embodiments of the generalized coil switching circuit 106 of FIG. 3. Fundamental requirements for these components include high current-carrying capacity and controllable, high-frequency switching.

A first particular embodiment of the generalized coil switching circuit 106 illustrated in FIG. 3 is shown with respect to FIG. 4. This embodiment utilizes switch implementations in which $S_1$ and $S_2$ are controllable, forward carrying, forward blocking switches such as Insulated Gate Bipolar Transistors (IGBTs) or power Metal Oxide Semiconductor Field Effect Transistors (MOSFETs), and $S_3$ and $S_4$ are forward carrying, reverse blocking elements such as diodes. The switches and blocking elements are operated in conformity with the generalized description of operation given above with respect to FIG. 3.

Control over operation of the controllable switches is provided according to well-known principles. For example, a programmable controller 202 having the appropriate output signal characteristics may be employed. Preferably, the controller 202 is provided with a user interface (represented by the arrow in the figure) which enables adjustments to be made to the timing and duration of the switch operations.

It will be appreciated by those of skill in the art that devices with similar operating characteristics can be utilized in place of these device selections. This particular embodiment provides significant operating flexibility. One IGBT module which is suitable for this embodiment is Part No. CM1000HA-24H from Powerex, Inc., Youngwood, Pa., a 1000 A, 1200 V IGBT. Modifying the coil 104 to include more turns as compared to that used with the Medtronic (Dantec) device described herein as prior art would enable higher-voltage, lower-current operation, which in turn would enable the use of lower cost IGBT modules rated for lower peak currents.

A second implementation 300 of the general concept described with respect to FIG. 3 is illustrated in FIG. 5. In this embodiment, $S_1$ is implemented as a semi-controllable (i.e. controllable turn on) device with forward carrying and blocking capability, such as a thyristor. $S_4$ is provided as a semi-controllable (i.e. controllable turn on) or controllable device with forward carrying and both forward and reverse blocking capabilities. For example, $S_4$ may be implemented as a thyristor (not shown), or as a series connection of a low-voltage power MOSFET and a diode (as illustrated in FIG. 5). The $S_4$ device must have full reverse blocking capability, but only requires low forward blocking capability. $S_2$ and $S_3$ in FIG. 5 are implemented as in the embodiment of FIG. 4. Operation of the circuit 106 is then carried out as described with respect to FIG. 3 through the use of the controller 302. A user interface to the control mechanism 302 (represented by the arrow in FIG. 5) may take the form of a data bus interface, a keyboard, or a graphical user interface (GUI), among other options.

The embodiment of FIG. 5 may be less expensive as compared to the embodiment of FIG. 4, based on contemporary component prices. Once the pulse is initiated, $S_2$ and $S_4$ may be modulated as described above (if desired) to control the rising current waveform. Once the capacitor C voltage reaches zero, $S_4$ may be left off until device $S_1$ recovers blocking capability, then $S_4$ and $S_2$ may be modulated as previously described for the falling portion of the pulse. Those skilled in the art will recognize that similar performance can be realized by an embodiment in which the switches $S_1$ and $S_2$ are interchanged, switches $S_3$ and $S_4$ are interchanged, and the modulation rules for the switches are adjusted accordingly; such an alternative embodiment 400 is illustrated in FIG. 6. As above, a control module 402 is provided to enable flexible control over the switch duty cycles and consequently the resulting coil waveform.

Constant or static duty-cycle operation is envisaged for less-expensive, simpler devices incorporating the presently disclosed invention. However, as described, control circuitry is preferably provided for the components of the coil switching circuit 106. Because the individual components employed in the various embodiments of the present invention have well-established control techniques, it is not necessary to describe in detail the design and interface of such control circuitry for use in controlling the respective components in the context of the presently disclosed invention.

These and other examples of the invention illustrated above are intended by way of example and the actual scope of the invention is to be limited solely by the scope and spirit of the claims.

We claim:

1. A magnetic stimulator system, comprising:
   a capacitor;
   a capacitor pre-charge circuit, in electrical communication with said capacitor, for selectively establishing an electric potential across said capacitor; and
   a coil switching circuit, in communication with said capacitor, comprising an inductive stimulator coil for generating a magnetic field in response to a current flow therethrough, said current resulting from dissipation of said electric potential across said capacitor, and a bridge circuit comprised of first and second half-bridge circuits, each of said half-bridge circuits having two respective switching elements in a serial arrangement and providing an output terminal in communication a respective end of said inductive stimulator coil.

2. The magnetic stimulator system of claim 1, wherein each switching element of said first half-bridge circuit is disposed to have an electrical forward direction towards said first half-bridge circuit output terminal, and
each switching element of said second half-bridge circuit is disposed to have an electrical forward direction away from said second half-bridge circuit output terminal.

3. The magnetic stimulator system of claim 1, wherein said two switching elements of said first half-bridge circuit are comprised of a first controllable switch serially connected to a forward carrying, reverse blocking element.

4. The magnetic stimulator system of claim 3, wherein said first controllable switch is a controllable, forward carrying, forward blocking switch.

5. The magnetic stimulator system of claim 4, wherein said controllable, forward carrying, forward blocking switch is selected from the group consisting of an insulated gate bipolar transistor (IGBT) and a power metal oxide semiconductor field effect transistor (MOSFET).

6. The magnetic stimulator system of claim 3, wherein said forward carrying, reverse blocking element is a diode.

7. The magnetic stimulator system of claim 1, wherein said first half-bridge circuit is comprised of a first semi-controllable switch serially connected to a forward carrying, reverse blocking element, and
said second half-bridge circuit is comprised of a first controllable switch serially connected to a second semi-controllable switch or a second controllable switch.

8. The magnetic stimulator system of claim 7, wherein each of said first and second semi-controllable switches is a controllable, forward carrying, forward blocking switch.

9. The magnetic stimulator system of claim 7, wherein each of said first and second semi-controllable switches is a thyristor.

10. The magnetic stimulator system of claim 7, wherein said forward carrying, reverse blocking element is a diode.

11. The magnetic stimulator system of claim 7, wherein said second semi-controllable switch or said second controllable switch of said second half-bridge circuit is a controllable, forward carrying, forward and reverse blocking switch.

12. The magnetic stimulator system of claim 7, wherein said second semi-controllable switch or said second controllable switch of said second half-bridge circuit is a thyristor.

13. The magnetic stimulator system of claim 7, wherein said second semi-controllable switch or said second controllable switch of said second half-bridge circuit is a series combination of a low-voltage power metal oxide semiconductor field effect transistor (MOSFET) and a diode.

14. A method of providing a desired current profile through a stimulus coil, comprising:
   providing a bridge circuit comprised of two half-bridge circuits, wherein a first of said half-bridge circuits is comprised of two serially arranged switching elements each having a forward direction towards a respective common node therebetween and wherein a second of said half-bridge circuits is comprised of two serially arranged switching elements each having a forward direction away from a respective common node therebetween;
   disposing said stimulus coil intermediate said common nodes of said first and second half-bridge circuits;
   providing a capacitor having a positive terminal in electrical communication with a first end of said first and second half-bridge circuits and a negative terminal in electrical communication with a second end of said first and second half-bridge circuits;
   providing a capacitor pre-charge sub-circuit in electrical communication with said capacitor;
   opening said switching elements of said bridge circuit;
   operating said pre-charge sub-circuit to pre-charge said capacitor to a first voltage level;
   selectively closing at least two of said switching elements to at least partially discharge said capacitor voltage across said stimulus coil;
   selectively closing and opening said switching elements to re-establish at least a portion of said first voltage level from said stimulus coil to said capacitor.

15. The method of claim 14, further comprising subsequent to said step of selectively closing and opening the step of operating said pre-charge sub-circuit to pre-charge said capacitor from said re-established voltage level to said first voltage level.

16. The method of claim 14, wherein said step of selectively closing at least two of said switching elements comprises selectively closing a first switching element of said first half-bridge circuit having one end in electrical commu nication with said capacitor positive terminal and selectively closing a first switching element of said second half-bridge circuit having one end in electrical communication with said capacitor negative terminal.

17. The method of claim 14, wherein said step of selectively opening and closing said switching elements comprises opening a first switching element of said first half-bridge circuit having one end in electrical communication with said capacitor positive terminal, closing a second switching element of said first half-bridge circuit having one end in electrical communication with said capacitor negative terminal, and selectively opening and closing said switching elements of said second half-bridge circuit.

18. The method of claim 14, wherein said step of selectively opening and closing said switching elements comprises opening a first switching element of said second half-bridge circuit having one end in electrical communication with said capacitor negative terminal, closing a second switching element of said second half-bridge circuit having one end in electrical communication with said capacitor positive terminal, and selectively opening and closing said switching elements of said first half-bridge circuit.

\* \* \* \* \*